US00PP25188P3

(12) United States Plant Patent
Madsen

(10) Patent No.: US PP25,188 P3
(45) Date of Patent: Dec. 23, 2014

(54) ***CAMPANULA* PLANT NAMED 'PKMP10'**

(50) Latin Name: ***Campanula portenschlagiana* Schult.**
Varietal Denomination: PKMP10

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 226 days.

(21) Appl. No.: 13/507,227

(22) Filed: Jun. 14, 2012

(65) Prior Publication Data

US 2013/0340139 P1 Dec. 19, 2013

(51) Int. Cl.
*A01H 5/00* (2006.01)

(52) U.S. Cl.
USPC ..... Plt./414

(58) Field of Classification Search
CPC ..... A01H 5/02; A01H 5/00
USPC ..... Plt./414
See application file for complete search history.

*Primary Examiner* — June Hwu
(74) *Attorney, Agent, or Firm* — Foley & Lardner LLP

(57) ABSTRACT

A new and distinct cultivar of *Campanula* plant named 'PKMP10', characterized by its compact plant habit; globular plant form; vigorous growth habit; upright dark violet flowers and small leaves.

9 Drawing Sheets

Latin name of genus and species of the plant claimed: *Campanula portenschlagiana* Schult.

Variety denomination: 'PKMP10'.

BACKGROUND OF THE INVENTION

The present invention relates to a new and distinct cultivar of *Campanula* plant, botanically known as *Campanula portenschlagiana* Schult., commonly known as Dalmatian Bellflower, and hereinafter referred to by the name 'PKMP10'.

The new *Campanula*, 'PKMP10', is a product of a planned breeding program conducted by the inventor, Christian Hald Madsen, in Søhus, Denmark. The new *Campanula* originated from a cross made by the inventor in August 2009 between a proprietary selection of *Campanula portenschlagiana* Schult. designated 08.08.1001 (breeder reference, unpatented) as the female parent and a proprietary selection of *Campanula portenschlagiana* Schult. designated 08.08.1001 (breeder reference, unpatented) as the male parent. The new *Campanula* 'PKMP10' was discovered and selected by the inventor in August 2010 as a single flowering plant within the progeny of the stated cross in a controlled environment in Søhus, Denmark. The inventor selected 'PKMP10' on the basis of its compact and freely flowering plant habit.

Asexual reproduction of the new *Campanula* cultivar by terminal cuttings in Søhus, Denmark has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMP10'. These characteristics in combination distinguish 'PKMP10' as a new and distinct cultivar:

1. Upright plant habit with short upright stems.
2. Bushy globular plant form.

3. Vigorous growth habit, but still needing less chemical growth retardation.
4. Small and dark violet flowers with wide and long petals.
5. Large quantity of buds.
6. No need for vernalization Plants of the cultivar 'PKMP10' can be compared to the *Campanula portenschlagiana* Schult. cultivar 'PKMP09' (patented, U.S. Plant Pat. No. 22,774). In side-by-side comparisons conducted by the inventor in Stige, Denmark, plants of the instant cultivar 'PKMP10' and plants of the cultivar 'PKMP09' differ in the following characteristics:

1. Plants of 'PKMP10' have smaller buds and flowers than plants of 'PKMP09'.
2. Plants of 'PKMP10' have a larger number of buds than 'PKMP09'.
3. Plants of 'PKMP10' have a darker stem color than plants of 'PKMP09'.

Plants of the cultivar 'PKMP10' can also be compared to the parent *Campanula portenschlagiana* Schult. cultivar 08.08.1001 (breeder reference, unpatented). Plants of the instant cultivar 'PKMP10' and plants of the parent cultivar 08.08.1001 differ in the following characteristics:

1. Plants of 'PKMP10' have darker flowers and buds than plants of '08.08.1001'.
2. Plants of 'PKMP10' are more upright and freely flowering than plants of '08.08.1001'.

BRIEF DESCRIPTION OF THE PHOTOGRAPHS

The accompanying colored photographs illustrate the overall appearance of the new *Campanula* 'PKMP10', showing the colors as true as it is reasonably possible to obtain in colored reproductions of this type. Colors in the photographs may differ slightly from the color values cited in the detailed botanical description, which more accurately describe the actual colors of 'PKMP10'.

FIG. 1 comprises a side perspective view of a typical flowering plant of PKMP10 grown in an 11 cm pot.

FIG. 2 comprises a close-up view of a typical young bud of PKMP10.

FIG. 3 comprises a close-up view of a typical mature bud of PKMP10.

FIG. 4 comprises a close-up side perspective view of a typical flower of PKMP10.

FIG. 5 comprises a close-up front perspective view of a typical flower of PKMP10.

FIG. 6 comprises a close-up view of a typical basal leaf of PKMP10.

FIG. 7 comprises a close-up view of a typical apical leaf of PKMP10.

DETAILED BOTANICAL DESCRIPTION

Figure 1:
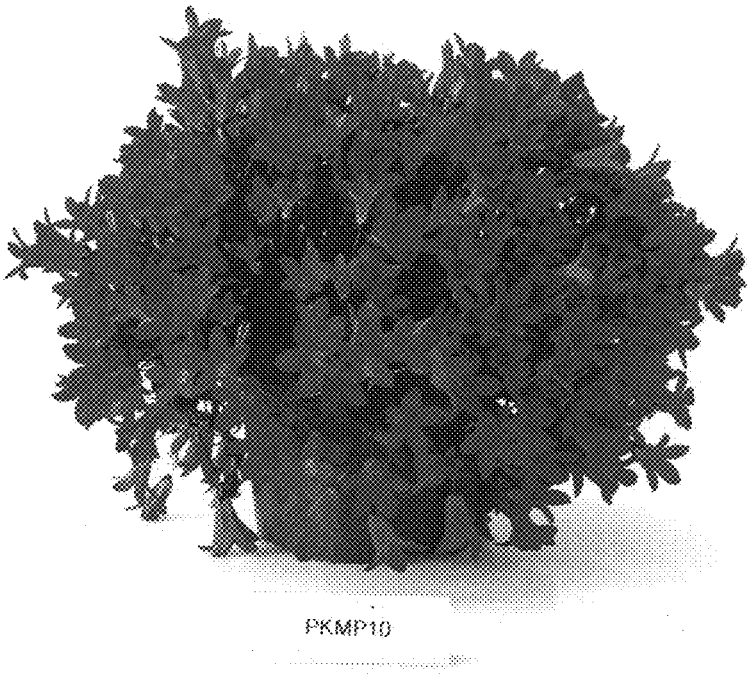
Figure 2:
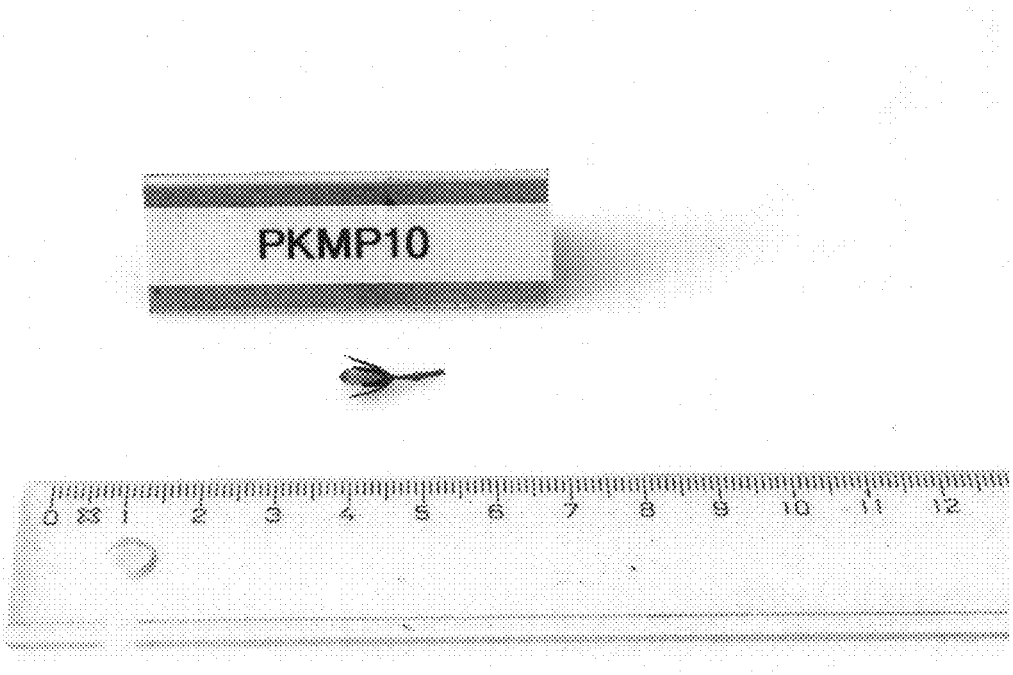
Figure 3:
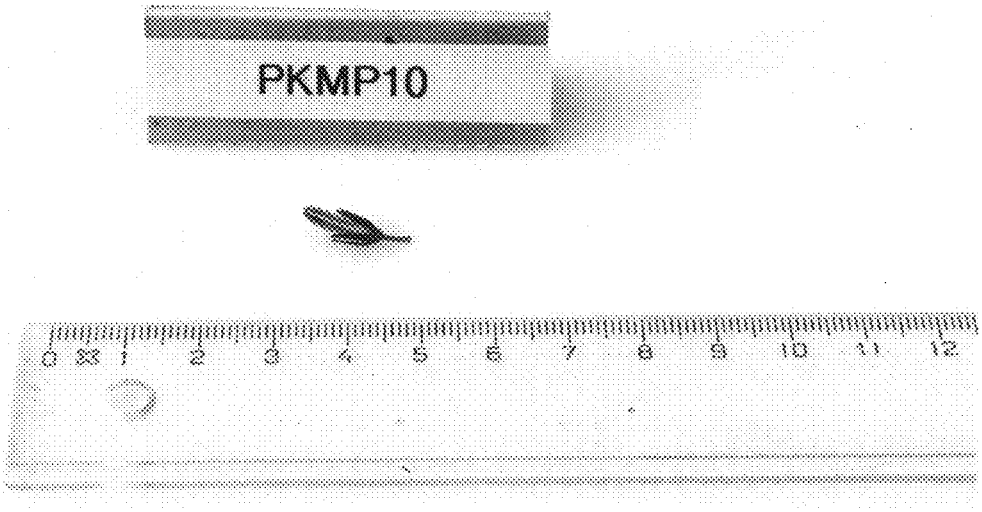
Figure 4:
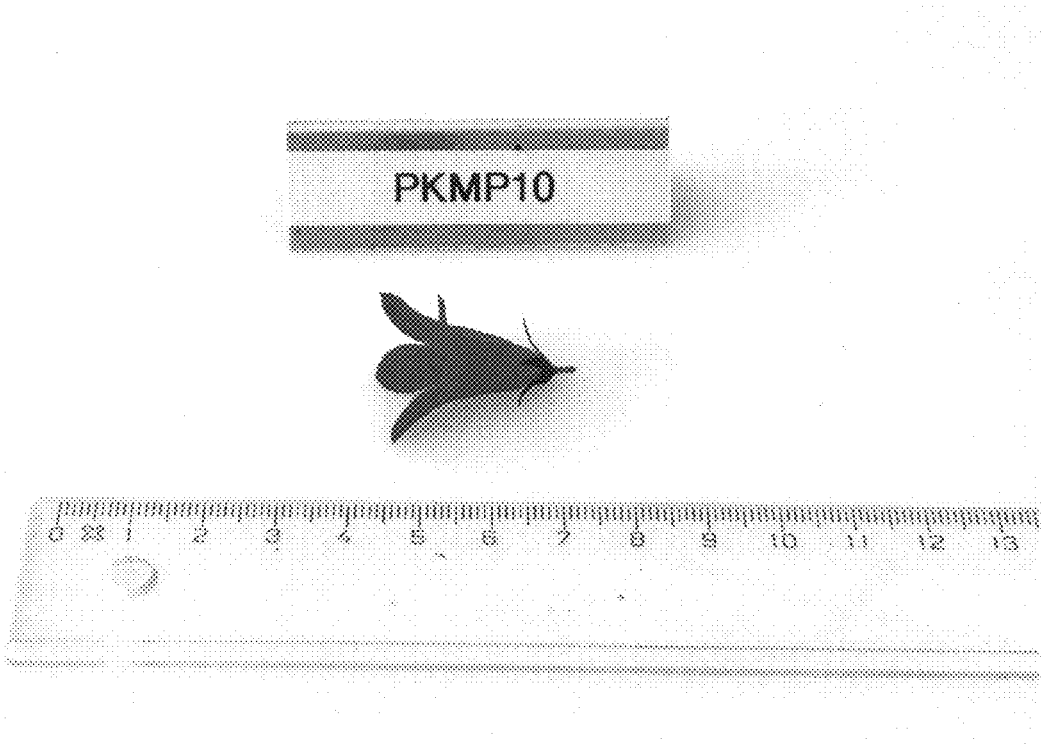
Figure 5:
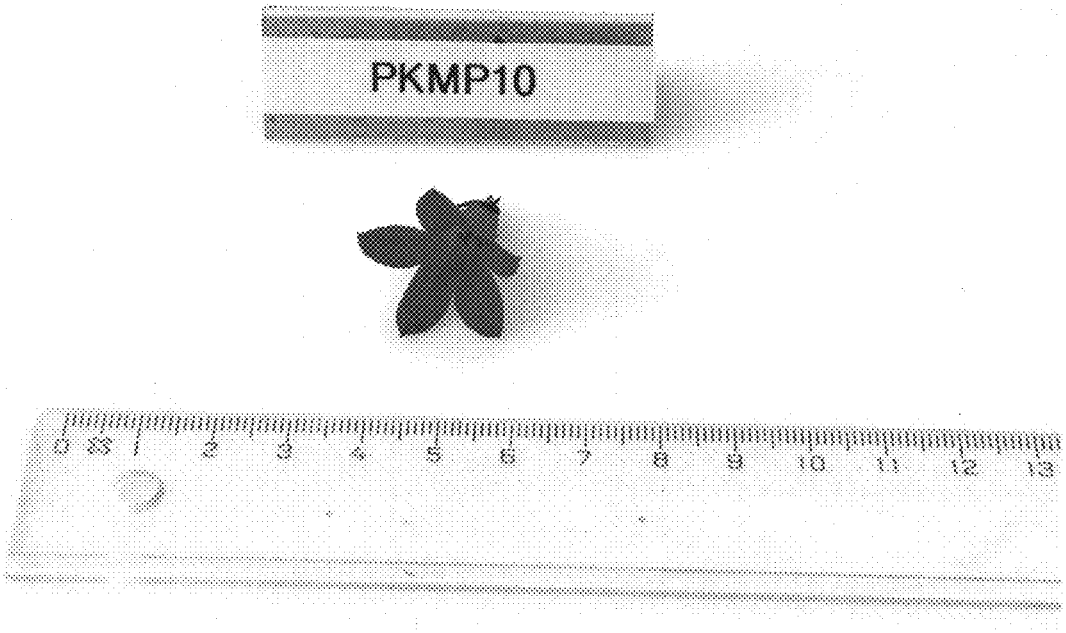
Figure 6:
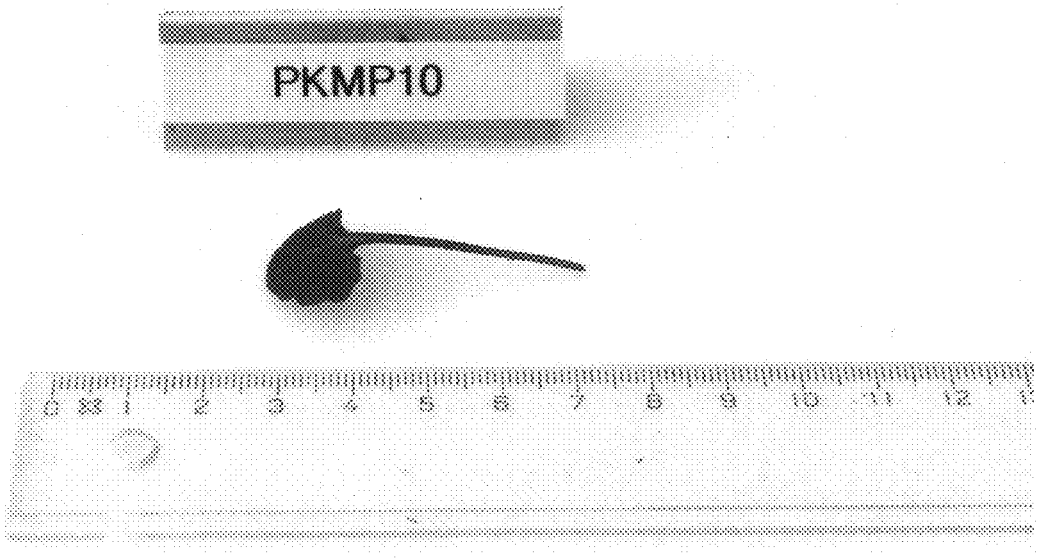
Figure 7:
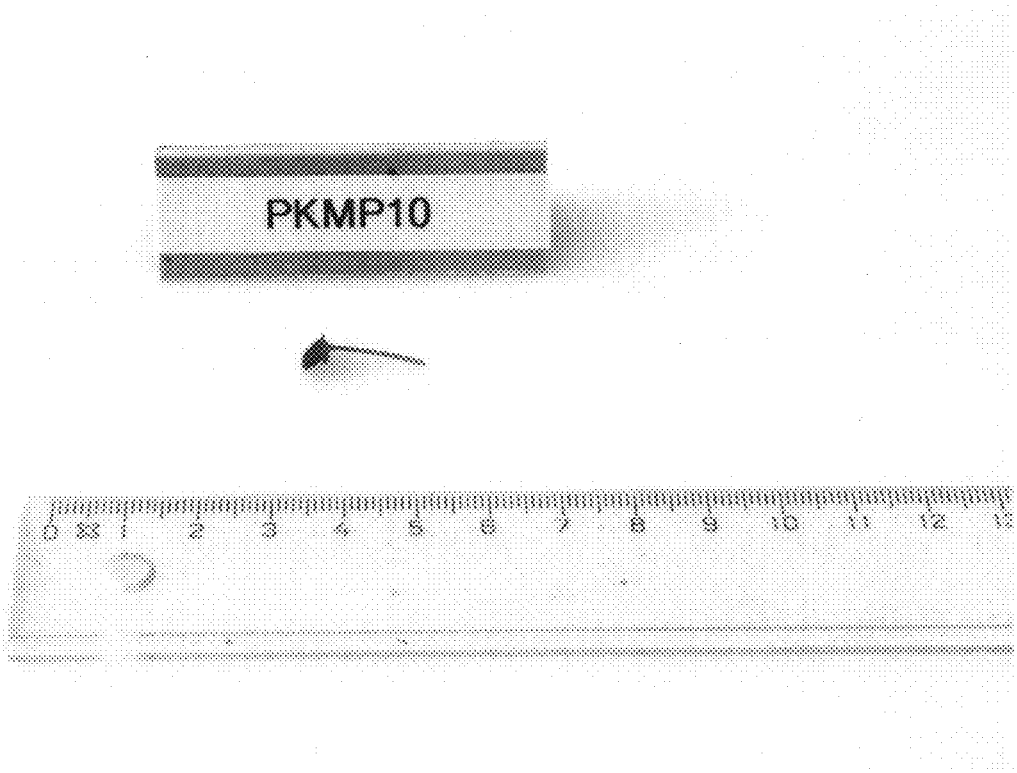
Figure 8:
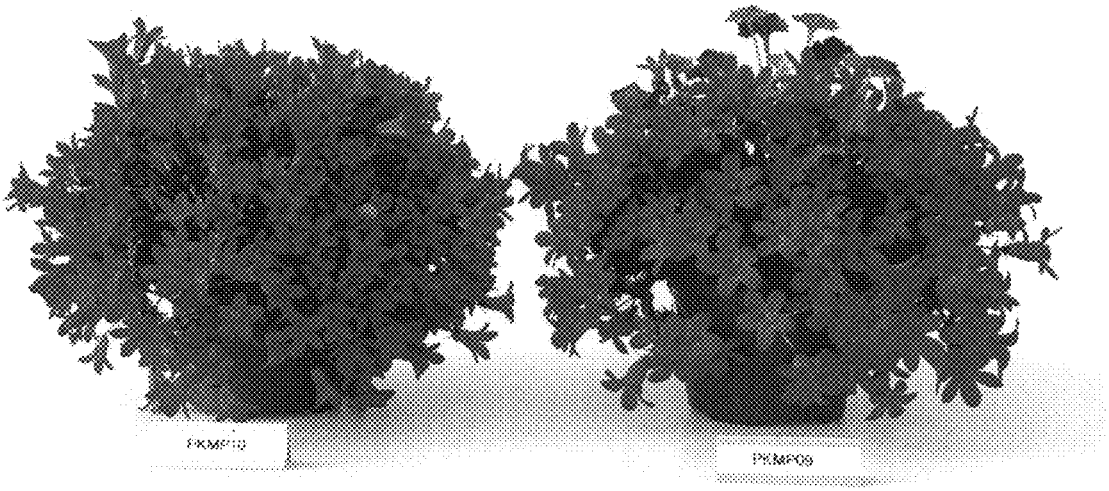
FIG. 8 is a comparison view of a typical flowering plant of PKMP10 with a typical flowering plant of PKMP09.
Figure 9:
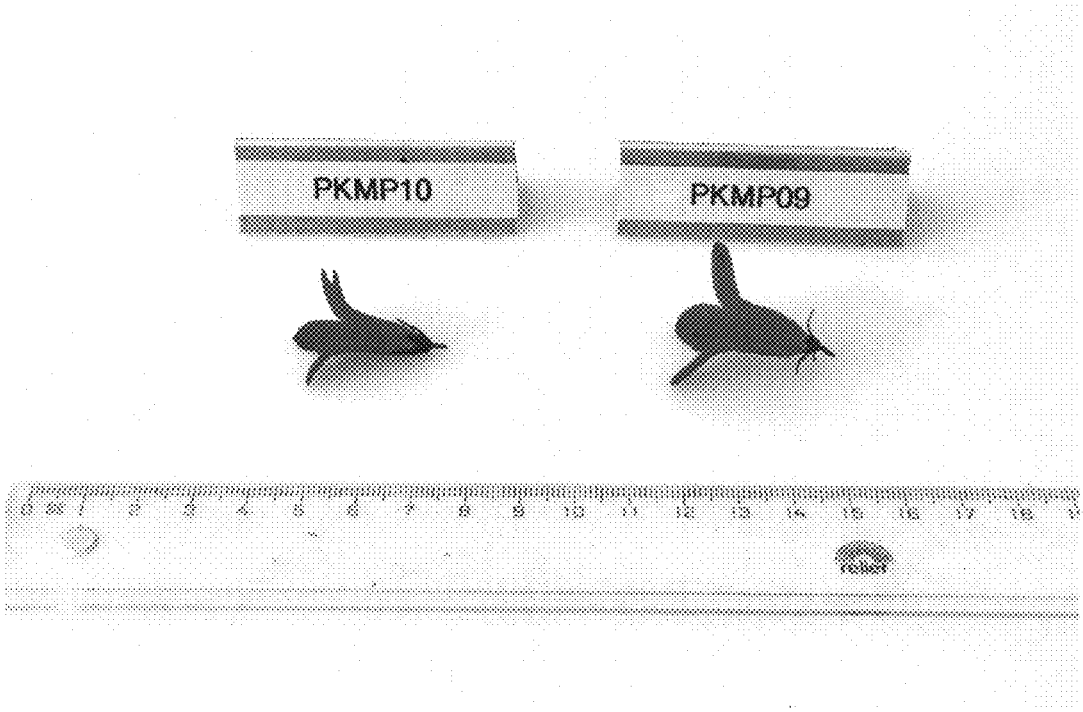
FIG. 9 is a comparison view of a typical flower of PKMP10 with a typical flower of PKMP09.

The new *Campanula* 'PKMP10' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKMP10' as grown under greenhouse conditions. No growth retardants were used.

The age of the 'PKMP10' plants described is 10 months after cutting. Color references are made to The Royal Horticultural Society Colour Chart (R.H.S.), $5^{th}$ edition, except where general colors of ordinary significance are used.

Classification:

*Botanical.*—*Campanula portenschlagiana* Schult.

Parentage:

*Female or seed parent.*—*Campanula portenschlagiana* Schult. designated 08.08.1001 (breeder reference, unpatented).

*Male or pollen parent.*—*Campanula portenschlagiana* Schult. designated 08.08.1001 (breeder reference, unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright plant habit. Campanulate flowers in racemes. Freely branching with lateral branches forming at every node; dense and bushy.

*Crop time.*—After rooting, about 14 weeks are required to produce finished flowering plants in 11 cm pots.

*Plant height* (*from soil level to top of plant plane*).—About 9 cm.

*Vigor.*—Vigorous growth rate.

*Stem.*—Length: 8-12 cm (including flowers). Shape: Round. Aspect: Center of Plant: Ascending. Perimeter: Spreading to drooping. Strength: Stiff. Color: RHS 137C, Green. Texture: Smooth. No pubescence.

Foliage description:

*Basal leaves.*—Leaf Shape: Cordate. Leaf Length: 15-17 mm. Leaf Width: About 20-22 mm. Apex: Rounded. Base: Cordate. Margin: Broadly dentate. Texture (both surfaces): Smooth, glabrous, dull. Color: Upper Surface, RHS N137A, Green. Lower Surface, RHS N137A, Green. Venation Color: Upper Surface, RHS N137A, Green. Lower Surface, RHS N137A, Green.

*Apical leaves.*—Leaf Shape: Cordate. Leaf Length: 10 mm. Leaf Width: 15 mm. Apex: Rounded. Base: Cordate. Margin: Broadly dentate. Texture (both surfaces): Smooth, glabrous, dull. Color: Upper Surface, RHS N137A, Green. Lower Surface, RHS N137A, Green. Venation Color: Upper Surface, RHS N137A, Green. Lower Surface, RHS N137A, Green.

*Petiole.*—Length: Basal leaves: 4-5 cm. Apical leaves: 0-1 cm. Diameter (Basal and Apical leaves): 1 mm. Color (Basal and Apical leaves): RHS N137A, Green.

Inflorescence description:

*Flower arrangement and shape.*—Single, upright, campanulate flowers in racemes, flowers with small star shaped calyx.

*Natural flowering season.*—Continuous throughout spring and summer. Season can be extended through long day treatments, no vernalization needed.

*Flower longevity.*—Longevity of individual flowers is highly dependent on temperature and light conditions. Flowers persistent.

*Buds* (*young and mature*).—Average quantity per lateral stem: 10-15. Length: 0-12 mm. Width (Diameter): 0-4 mm. Shape: Oblong; ridged. Color: Young: RHS 144D, Yellow-green at base, RHS N88C, Violet at tip. Mature: RHS N88A, Violet.

*Inflorescence size.*—Length: 5-7 cm. Width (Diameter): 6 cm.

*Average number per lateral stem.*—12-16.

*Flowers.*—Length: About 20 mm. Diameter: About 23 mm.

*Petals.*—Overall Shape: Lanceolate, acute. Length: 8-10 mm. Width: Base of lobe 6 mm. Average number per flower: 5. Arrangement: Single, sympetalous, campanulate. Petals basally fused. Texture (both surfaces): Velvety. Margin: Entire. Apex: Acute. Base: Fused.

*Corolla color.*—Upper and Lower surfaces, RHS N87A, violet. The bottom of the bell has the same color. Color does not fade.

*Sepals.*—Appearance: Shiny, glabrous. Arrangement: Free. Quantity per flower: 5. Length: 3-5 mm. Width: 1 mm. Overall shape: Arrow-shaped. Tip: Cuspidate. Base: Fused. Margin: Entire. Texture (both surfaces): Pubescent at the margins; very small hairs which can only be seen through magnification. Color (mature and immature): Upper and lower surfaces: Green, RHS 137A. Pedicel: Strength: Average. Length: About 27 mm. Diameter: About 1 mm. Color: RHS 137C, Green. Peduncles: None.

Reproductive organs:

*Androecium.*—Stamen number: 5, fused until pollen has been shed. Anther: Shape: Fused; curling after shedding. Length: 1 mm. Color: RHS 158B, Yellow-white. Filament: Length: 1 mm. Color: Whitish-green and generally covered by pollen; too small to determine RHS value. Pollen: Amount: Average. Color: RHS 158B, Yellow-white.

*Gynoecium.*—Pistil: Number: 1. Length: 10 mm. Stigma: Shape: Tripartite. Color: RHS N85A, violet. Style: Length: 9 mm. Color: RHS N85A, violet. Ovary: Shape: Obovate; ribbed. Color: RHS 1C, Green-yellow.

Pest/disease resistance/susceptibility: None observed to date.
Seed/fruit: None observed.
Weather tolerance: Plants of the new *Campanula* have exhibited good tolerance to drought, rain and wind, with low temperature resistance to −15° C.

I claim:

1. A new and distinct cultivar of *Campanula* plant named 'PKMP10', as illustrated and described herein.

* * * * *